(12) United States Patent
Gorochow

(10) Patent No.: US 10,517,708 B2
(45) Date of Patent: Dec. 31, 2019

(54) MULTI-BASKET CLOT CAPTURING DEVICE

(71) Applicant: DePuy Synthes Products, Inc., Raynham, MA (US)

(72) Inventor: Lacey Gorochow, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 353 days.

(21) Appl. No.: 15/334,984

(22) Filed: Oct. 26, 2016

(65) Prior Publication Data

US 2018/0110606 A1    Apr. 26, 2018

(51) Int. Cl.
*A61F 2/01* (2006.01)
*A61B 17/22* (2006.01)

(52) U.S. Cl.
CPC .............. *A61F 2/013* (2013.01); *A61B 17/22* (2013.01); *A61B 2017/22034* (2013.01); *A61F 2002/011* (2013.01); *A61F 2002/016* (2013.01); *A61F 2230/0023* (2013.01); *A61F 2230/0054* (2013.01); *A61F 2230/0086* (2013.01)

(58) Field of Classification Search
CPC ................................. A61F 2/013; A61B 17/22
See application file for complete search history.

(56) References Cited

U.S. PATENT DOCUMENTS

| | | | |
|---|---|---|---|
| 6,485,502 B2 | 11/2002 | Don Michael et al. | |
| 7,214,237 B2 | 5/2007 | Don Michael et al. | |
| 8,088,140 B2 | 1/2012 | Ferrera et al. | |
| 8,945,172 B2 | 2/2015 | Ferrera et al. | |
| 9,351,749 B2 | 5/2016 | Brady et al. | |
| 9,358,022 B2 | 6/2016 | Morsi | |
| 2002/0072764 A1* | 6/2002 | Sepetka | A61B 17/22031 606/200 |
| 2005/0038447 A1* | 2/2005 | Huffmaster | A61B 17/221 606/127 |
| 2006/0015136 A1 | 1/2006 | Besselink | |
| 2007/0078481 A1 | 4/2007 | Magnuson | |
| 2011/0213403 A1 | 9/2011 | Aboytes | |
| 2012/0116443 A1 | 5/2012 | Ferrera et al. | |

(Continued)

FOREIGN PATENT DOCUMENTS

| WO | 2010/102307 A1 | 9/2010 |
|---|---|---|
| WO | 2014/055609 A1 | 4/2014 |

OTHER PUBLICATIONS

Extended European Search Report dated Jan. 23, 2018 during the prosecution of European Patent Application No. 17198329.9.

*Primary Examiner* — Richard G Louis
(74) *Attorney, Agent, or Firm* — Troutman Sanders LLP

(57) ABSTRACT

A multi-basket clot capturing device that includes a distal basket connected to a wire. The distal basket may be positionable distal of the clot and operable to capture a distal portion of a clot. A proximal basket may be connected to a hypotube that is slidably axially connected to the wire. The proximal basket may be positionable proximal of the clot and operable to capture a proximal portion of the clot. A cage can form between the proximal and distal baskets around multiple portions of the clot for capturing the clot. Sliding the wire distally, or microcatheter proximally, relative to the clot causes the distal basket to move from a collapsed state to an expanded state. The cage may be around at least two portions of the clot that are opposed.

7 Claims, 9 Drawing Sheets

(56) References Cited

U.S. PATENT DOCUMENTS

| | | |
|---|---|---|
| 2013/0197567 A1 | 8/2013 | Brady et al. |
| 2013/0345739 A1 | 12/2013 | Brady et al. |
| 2014/0200608 A1 | 7/2014 | Brady et al. |
| 2014/0249565 A1* | 9/2014 | Laine ............ A61F 2/013 606/200 |
| 2015/0196744 A1 | 7/2015 | Aboytes |
| 2015/0223829 A1 | 8/2015 | Aboytes |
| 2015/0265299 A1* | 9/2015 | Cooper ............ A61B 17/221 606/200 |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0206344 A1 | 7/2016 | Bruzzi et al. |

* cited by examiner

210 — Move the wire connected to the distal basket distal of the clot and expose the distal basket from the microcatheter.

220 — Move the wire until the distal basket captures the clot.

230 — Move the microcatheter thereby exposing the proximal basket

240 — Move the wire until contacting the distal end of the hypotube forming a full cage around the clot.

250 — Capture and remove the clot out of the vasculature.

| 310 | Expanding the frame of a basket about a portion of a clot, the frame being slidably axially connected to a hypotube and a wire by: |

| 320 | Sliding outwardly a distal end of the hypotube along the wire when the frame is collapsed |

| 330 | Spokes that are pivotally connected between the hypotube and struts of the basket are pivoted radially outward from the hypotube as the hypotube slides along the wire in a predetermined direction |

MULTI-BASKET CLOT CAPTURING DEVICE

FIELD

The present disclosure relates generally to medical devices for treating an embolus or blood clot in a blood vessel.

BACKGROUND

One common way for a blood vessel to become obstructed is from deposition of clot inside the lumen of the blood vessels. A clot is understood throughout this application as a product of a blood coagulation in hemostasis. Clots can restrict the antegrade blood flow through the lumens of these blood vessels to the body tissues. To that end, any blockage or obstruction of a blood vessel can lead to many serious medical complications. For example, tissue may become damaged due to the decrease in the oxygen that often results from the obstructions in the vessel. Similarly, brain circulation can be affected and result in an ischemic stroke.

In order to restore flow restoration, the clot needs to be removed from the vasculature. Current clot retrieval devices on the market are constructed of a single tube that acts to retrieve a blood clot by enrapturing the clot through the struts of the stent. Such devices then drag the blood clot through the vasculature and out of the body.

Unfortunately, such approaches can only capture clots from a single tube or catheter and/or from a single side that in turn rely upon the outward force of the stent, and the ability of the struts to latch onto and entrap the clot. The problem with these types of retrievers is that they entrap the clot from the inside of the clot, and not from the outside. Capturing the clot from the inside can present difficulties for several reasons. Most notably, as the clot adheres to the vessel wall, the single-tube device may not have enough force to grasp the clot off of its wall.

Other known approaches have suffered from using fixed basket shapes or delivering baskets to a region of interest in the vasculature unsafely, such as U.S. Pat. Pub. 2015/0265299A1 to the University of Toledo or U.S. Pat. No. 9,358,022 to Inoha LLC. For example, these disclosures deliver a first fixed basket proximally relative to the clot and then deliver a second fixed basket distal of the clot. During positioning of the second fixed basket, however, these approaches tend to puncture the clot and risk injury to the patient by permitting particles dislodged from the clot to enter the flow of blood in the vasculature.

Previously known solutions have therefore depended on factors such as material, size, cell design, pre-determined basket size, unsafe deliveries, and internal friction of the clot retrievers. Previous approaches have also focused heavily on extra manipulation by the end-user to precisely, safely, and reliably arrange and position the clot capturing devices within the vasculature without rupturing the vessel wall or allow particles of the clot to enter the flow of blood in the vasculature. In turn, success and safety has relied heavily on end-user accuracy during delivery. Such approaches therefore unnecessarily increase risk of injury to the patient. Moreover, such clot capturing devices can be difficult to recapture after being delivered and/or deployed to vasculature areas of interest further risking detrimental effects of brain and/or cardiac function, including fatality, can result.

Therefore, prior approaches for removal of such clots have suffered from being too intrusive, unsafe, lack control and exert too much pressure on the vessel itself. Accordingly, there remains a need for new devices to safely and effectively remove an obstructing clot within the blood vessel wall.

SUMMARY

In some aspects, the present disclosure relates to a multi-basket clot capturing device that includes a distal basket connected to a wire. The distal basket may be operable to capture a distal portion of a clot. A proximal basket may be connected to a hypotube that is slidably axially connected to the wire. The proximal basket may be operable to capture a proximal portion of the clot. A cage can form between the proximal and distal baskets around multiple portions of the clot for capturing the clot. Moving from collapsed to expanded states may be accomplished by moving the microcatheter proximally relative to the clot or by moving the guide wire or hypotube distally relative to the clot.

In some examples, the cage forms around at least two portions of the clot that are opposed. The distal and/or proximal baskets can include a closed end opposite an open end. A frame of the respective basket may be defined between the closed and open end thereby forming a chamber or void operable to capture a portion of the clot (e.g. the distal portion or proximal portion of the clot). The frame may also be adjustable between a plurality of sizes or be constructed from material that conforms to the size and shape of the clot.

A microcatheter may be included with the multi-basket clot capturing device, the microcatheter being deliverable to a region of interest in the vasculature. In this regard, the hypotube and the wire may be slidably axially within the microcatheter. Moving the wire distally away from the microcatheter can cause the distal basket to move from a collapsed state to an expanded state so the frame of the distal basket is capable of capturing a distal portion of the clot. In certain embodiments, moving the microcatheter proximally, away from the distal basket, can cause the proximal basket to move from a collapsed state to an expanded state whereby the proximal basket is capable of capturing a proximal portion of the clot opposite the distal portion of the clot.

In certain examples, a plurality of struts of the distal basket are included that are operable to capture the clot. A plurality of spoke members can be pivotally connected between the struts and a distal end of the hypotube. In this respect, moving the hypotube distally can cause the spoke members to expand the distal basket. A plurality of interstices can be formed from or between the struts. The spoke members may be formed by cutting or etching into the hypotube. The spoke members may also be removably attached to the hypotube. The spoke members may be radially spaced about the hypotube. In certain examples, the hypotube may be axially connected to the proximal basket. The wire may also be axially connected to the distal basket.

In other examples, a method is disclosed for removing a clot from vasculature of a patient. The method may include some or all of the following steps: introducing a multi-basket clot capturing device into a region of interest of the vasculature distal of the clot, the device comprising a distal basket connected to a wire and a proximal basket connected to a hypotube that is axially and slidably connected to the wire, the distal basket being operable to capture a distal portion of the clot; moving the wire connected to the distal basket distal to the clot thereby causing the distal basket to expand away from a microcatheter connected to the wire and hypotube; moving the wire until the distal basket captures the distal portion of the clot; moving the microcatheter proximally causing a proximal basket of the clot capturing device to expand, the proximal basket being operable to capture a proximal portion of the clot; moving the wire connected to the distal basket until contacting a distal end of the hypotube forming a cage around the clot between the proximal and distal baskets.

The method may also include: removing the clot from the region of interest of the vasculature; forming a plurality of interstices on the distal and/or proximal baskets for capturing the clot; pivotally connecting a plurality of spoke members of the hypotube to a plurality of struts of the distal basket; and/or moving the hypotube towards the distal basket away from the microcatheter, while keeping the wire connected to the distal basket in place, thereby causing the distal basket to expand. The method may also include: forming a plurality of interstices from the struts; forming the spoke members by cutting or etching into the distal end of the hypotube; radially spacing the spoke members about the hypotube. The method may also include attaching the spokes to the distal basket by glue, welding, adding a hinge joint between one or more strut of the distal basket and a respective spoke of the hypotube. The method may also include axially connecting the hypotube to a central vertex of the proximal basket; and/or axially connecting the wire to a central vertex of the distal basket.

A method for deploying a basket of a multi-basket clot capturing device is also disclosed. The method can include expanding a frame of a first basket about a first portion of a clot, the frame being slidably axially connected to a hypotube and a wire, the frame being expanded by: sliding outwardly a distal end of the hypotube about the wire when the frame is collapsed and aligned with the hypotube and wire; and radially pivoting a plurality of spokes attached between a distal end of a hypotube and a plurality of struts of the basket.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 11 is a schematic overview of one example method of deploying an exemplary dual basket device into vasculature of a patient.

FIG. 12 is a schematic overview of another example method of deploying an exemplary dual basket device into vasculature of a patient.

DETAILED DESCRIPTION

Figure 1:
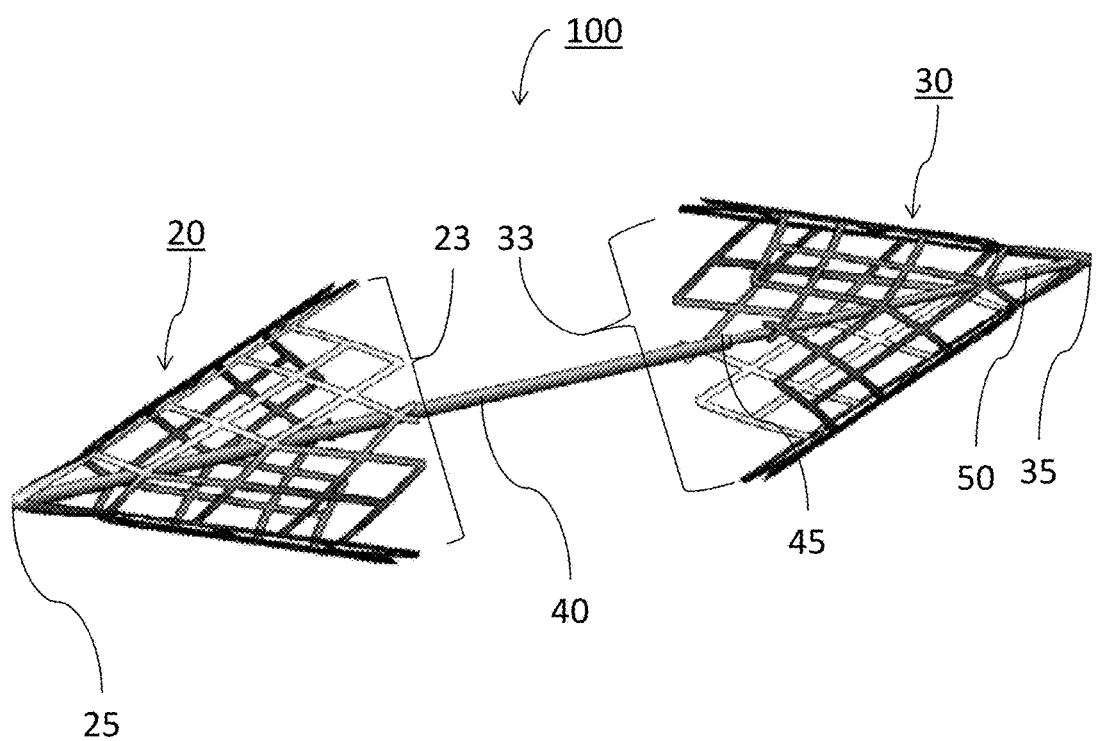
FIG. 1 is a perspective view of an example of the dual basket device.

Although examples of the disclosed technology are explained in detail herein, it is to be understood that other examples are contemplated. Accordingly, it is not intended that the disclosed technology be limited in its scope to the details of construction and arrangement of components set forth in the following description or illustrated in the drawings. The disclosed technology is capable of other examples and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing examples, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated delivery of microcatheter(s) and removal of clots from vasculature of a subject.

The herein disclosed clot capturing device 100 resolves known problems in the field by providing a multi-tubed, multi-basket approach that adjustably and safely captures the clot from multiple opposed sides. In certain examples, device 100 is operable to capture a clot that is in a blood vessel from outside of the clot 10, meaning, from opposite sides of the same clot 10. It is understood that device 100 is capable of being used within a blood vessel having diameters ranging between 2 and 5.5 mm approximately. However, the device 100 is not so limited and device 100 may be scaled for use within any vasculature as needed or required.

FIG. 1 more clearly shows device 100 in a perspective view of an example embodiment where device 100 is a dual-basket device having a distal basket 30 and a proximal basket 20. The distal basket 30 may be operable to capture a distal portion of the clot 10 whereas the proximal basket 20 may be operable to capture a proximal portion of the clot 10.

Baskets 20 and 30 may be axially aligned and connected through a hypotube 40 and wire 50. Hypotube 40 may be slideably inserted over wire 50 though device 100 is not so limited and wire 50 may be slideably inserted over hypotube 40. As described more particularly below, moving hypotube 40 and/or wire 50 may in turn cause corresponding baskets 20 and 30 to move from collapsed states to one or more expanded states. In certain examples, only one expanded state may exist for each basket or one or both baskets 20 and 30 may be adjusted between a plurality of different expanded states according to the size of the clot 10.

Figure 2:
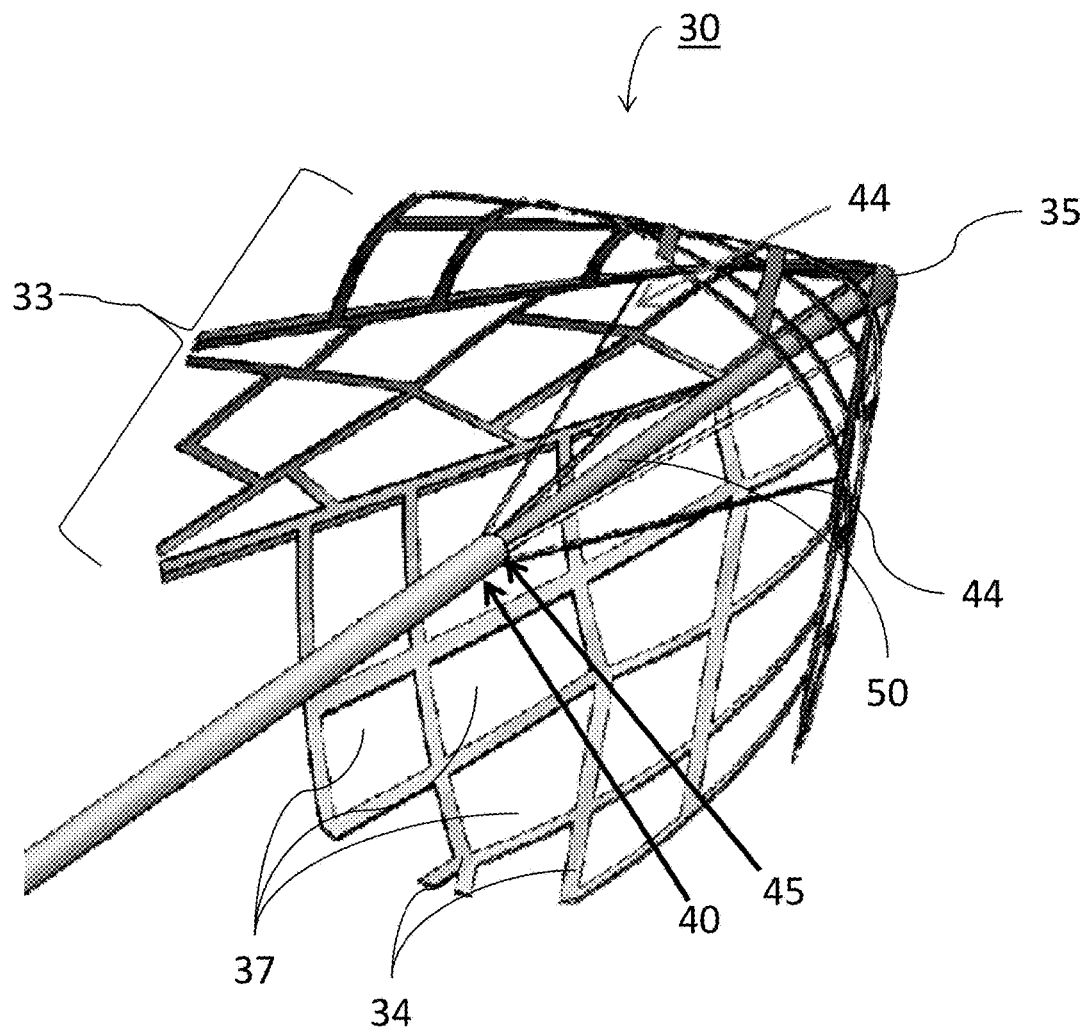
FIG. 2 is a perspective view of an exemplary distal basket.

As can be seen in FIGS. 1 and 2, the distal basket 30 may have a frame that includes a closed distal end defined by central vertex 35 and an open proximal end 33. The cavity or void of basket 30 in certain examples can be formed by open end 33, a plurality of struts 34, and interstices 37 formed therebetween. Struts 34 may be separately assembled with each other, integrally formed from a single piece, or some combination thereof. In FIG. 2, a perspective close-up view of basket 30 is shown in communication with hypotube 40 slideably inserted over wire 50. One or more of the struts 34 can be pivotally attached to respective spokes 44 of hypotube 40. As shown, one or more spokes 44 may be radially spaced about hypotube 40, wherein a respective spoke 44 can be attached to a distal end of hypotube 40 to form a hypotube-wire junction 45. Each spoke 44 may be pivotable so that as hypotube 40 is caused to slide along wire 50, strut 34 causes basket 30 to expand by urging open corresponding spokes 44 of the frame of basket 30.

This slidable, pivoting expansion can be best understood with how a conventional umbrella moves from being collapsed to expanded. The distal basket 30 may be axially aligned and attached to wire 50 at its central vertex 35. The distal basket 30 may also be fastened to hypotube 40 (e.g. being threaded thereto) to which the proximal basket 20 is attached on the opposite, proximal portion of hypotube 40 as shown in FIG. 1. The void or chamber of distal basket 30 that is formed by its frame defined by open end 33, struts 34 and interstices 37 can be used to externally capture the distal portion of the clot 10 and remove the clot 10 off of the vessel wall. This approach is particularly advantageous since it permits basket 30 and its corresponding void or chamber be controlled by spokes 44 for expansion between one of a plurality of different diameters at end 33 or across different portions of basket 30 to affect both void size and frame shape as described more particularly below.

Figure 3:
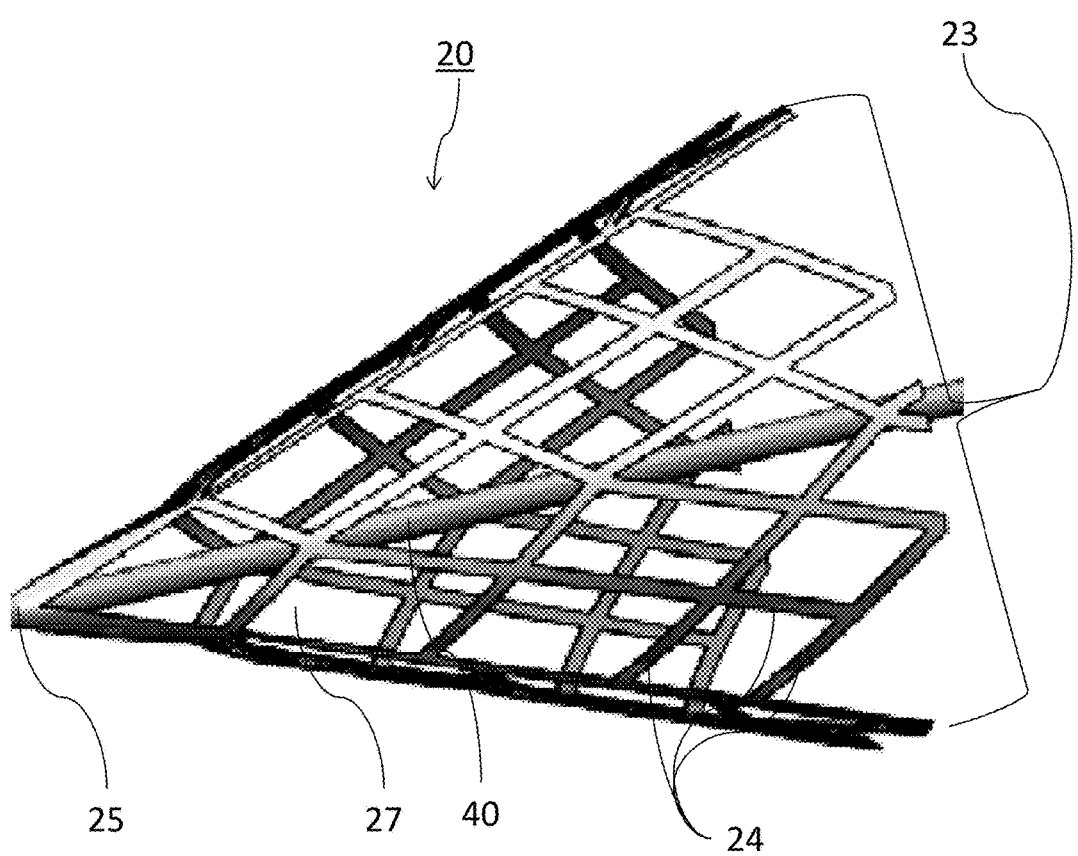
FIG. 3 is a perspective view of an exemplary proximal basket.

Turning to FIG. 3 is a close-up perspective view of proximal basket 20. Similar to distal basket 30, proximal basket 20 may be axially connected to the opposite portion of hypotube 40 at its central vertex 25. As shown, basket 20 may be closed at central vertex 25 and opened at its opposite open end 23. The proximal basket 20 may also include a frame that includes open end 23, a plurality of struts 24, and corresponding interstices 27 that together form a void or chamber operable to capture the opposite, proximal portion of the clot 10. Struts 24 may be separately assembled with each other, integrally formed from a single piece, or some combination thereof. During deployment, the proximal basket 20 may be positioned with respect to the proximal portion of clot 10 so that respective ends 23 and 33 communicate to form cage 60 around clot 10 (see FIGS. 4-8). In some examples, ends 23 and 33 may be operable to removably attach to each other through one or more removable fasteners (e.g. one or more bolts, clamps, cables, couplings, dowels, hooks, joints, keys, latches, nuts, pins, magnets, click-fit connectors, hook and loop fasteners, etc.). A volume or shape of cage 60 may be adjustable or conformable to various sized clots. The proximal basket 20 can therefore be used to encase the proximal portion of the clot 10 so that the entire clot 10 is enclosed therein as the clot 10 is traveling through the increasingly larger vasculature.

Each basket 20 and/or 30 can be made of rigid material such as Nitinol and formed (e.g. heat set) to include a cavity, chamber, or void operable to capturing and retaining a blood clot therein (e.g. a basket shape). When assembled, device 100 can be activated between collapsed and deployed states. For example, in a collapsed state one or both basket can be stowed in or along hypotube 40 and wire 50 of device 100. In contrast, in a deployed state, baskets 20 and/or 30 may be moved along hypotube 40 and/or wire 50 to slide therealong and expand until forming its respective void or chamber.

Specifically, hypotube 40 can be attached to the proximal basket 20 and may be cut to create spokes 44 that can be attached to struts 34 of the distal basket 30. The hypotube 40 can be moved (e.g. pushed) relative to a wire 50 that is axially and/or slidably connected therewith as shown particularly in FIG. 2. To collapse the distal basket 30, the hypotube 40 can be pulled relative to the wire 50, thus moving the spokes 44 inward, and collapsing the basket 30 as shown more particularly below in FIG. 2. The basket 30 may be grafted with a polymer to aid in covering and capturing more of the clot 10.

Figure 4:
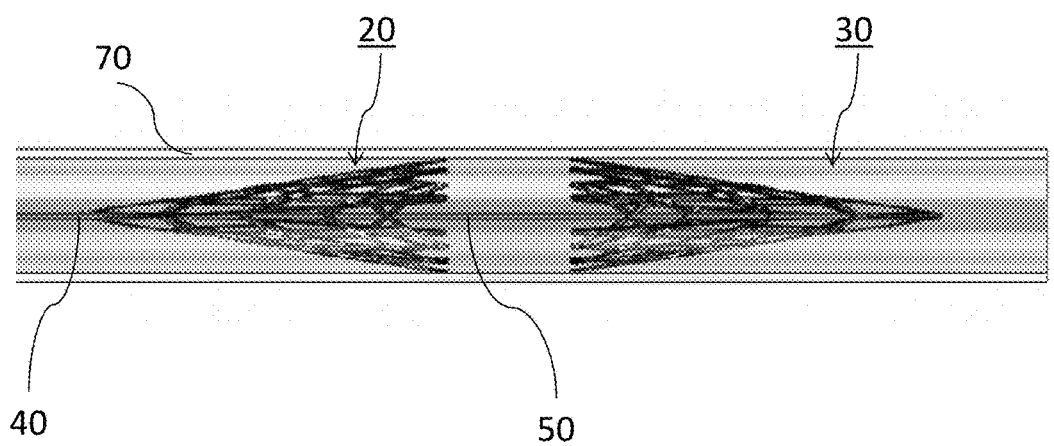
FIG. 4 is a view of an exemplary dual basket device when collapsed in an exemplary microcatheter.

Turning to FIGS. 4-8 is an exemplary depiction of device 100 being assembled through a series of steps around clot 10 with baskets 20 and 30. Specifically, baskets 20 and 30 can be seen moving between collapsed in microcatheter 70 to expanded states capable of capturing respective portions of clot 10. In FIG. 4, baskets 20 and 30 can be seen collapsed within microcatheter and ready for deployment to a region of interest in the vasculature to capture clot 10. Basket 30 may be capable of sliding distally along hypotube 40 and/or wire 50 to initiate distal deployment of basket 30.

Figure 5:
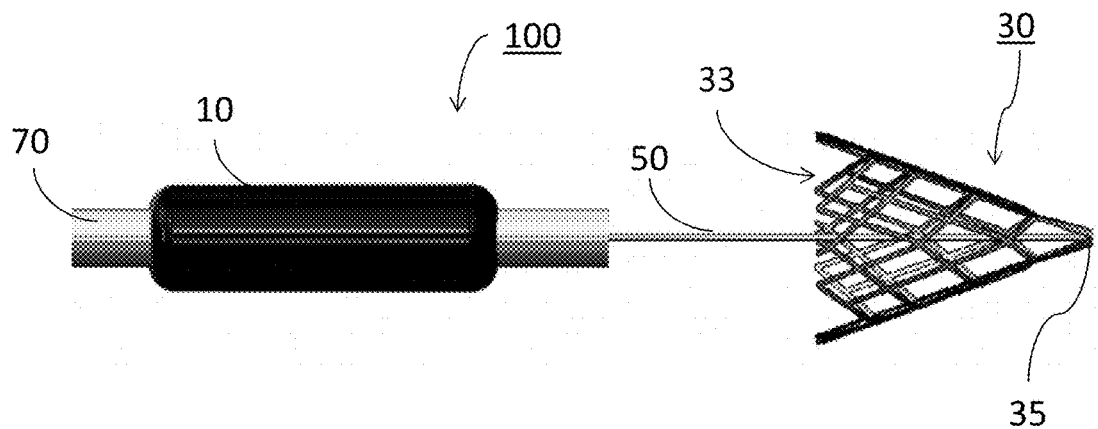
FIG. 5 depicts a side plan view of an exemplary dual basket device prior to capturing a blood clot.

In FIG. 5, a side plan view of device 100 can be seen being positioned for use with hypotube 40 and wire 50. Microcatheter 70 as previously shown in FIG. 4 has now been delivered to the region of interest of the vasculature through so that hypotube 40 and wire 50 may slideably move relative to each other to deploy respective baskets 20 and 30. It can be seen that hypotube 40 and wire 50 may be axially and/or slideably connected to each other as well as microcatheter 70.

Distal basket 30 may be deployed and moved distally from a collapsed state within microcatheter 70 to an expanded stated with its basket chamber ready for capturing a distal portion of clot 10. As previously described, positioning basket 30 distal of clot 10 in this manner without puncturing clot 10 is particularly advantageous as this can provide an added level of safety. Whereas prior approaches have punctured or otherwise contacted clot 10 during removal, this distal deployment of basket 30 prevents any particles from being dislodged from clot 10 during delivery and entering the bloodstream. The only puncturing, if any, would be caused by the initial microcatheter 70 puncturing the clot 10. Basket 30 may be deployed to the expanded stated by moving and/or sliding forward wire 50 relative to hypotube 40 to cause spokes 44 to pivot outwards the frame of basket 30. It is understood that any other mode of expansion can be used to move basket 30 from its collapsed to expanded states and/or multiple settings of basket 30's frame may be used for varying sized basket chambers or voids to correspond to similarly sized clots. Once deployed from the microcatheter 70, the distal basket 30 can be seen distal of the clot ready to adhere, contact, capture, or otherwise communicate with the distal portion of clot 10. In certain examples, the distal basket 30 can be expanded and/or collapsed completely or partially back into the microcatheter 70.

Figure 6:
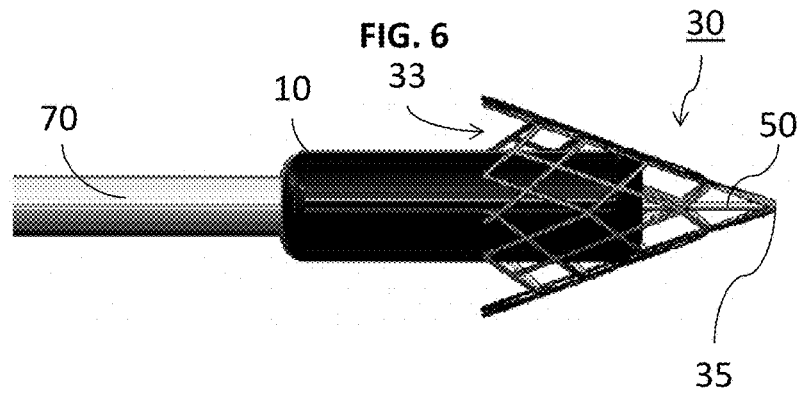
FIG. 6 depicts a side plan view of the device of FIG. 5, wherein the distal basket is deployed and in contact with the blood clot.

In FIG. 6, wire 50 can be seen having been moved (e.g. pulled back) causing basket 30 and its corresponding chamber to contact and capture the distal portion of clot 10. It can be understood any particles dislodged from clot 10 will be captured by basket 30 and that the frame of basket 30 in FIGS. 4-8 may be relatively angled or triangular. Device 100 is not so limited, however, and the frame of either basket 20 or 30 can be rounded (e.g. elliptical, hemispherical, etc.), rectangular, or any other shape as desired or needed that is operable to surround and capture a respective portion of clot 10 when moved into contact.

Figure 7:
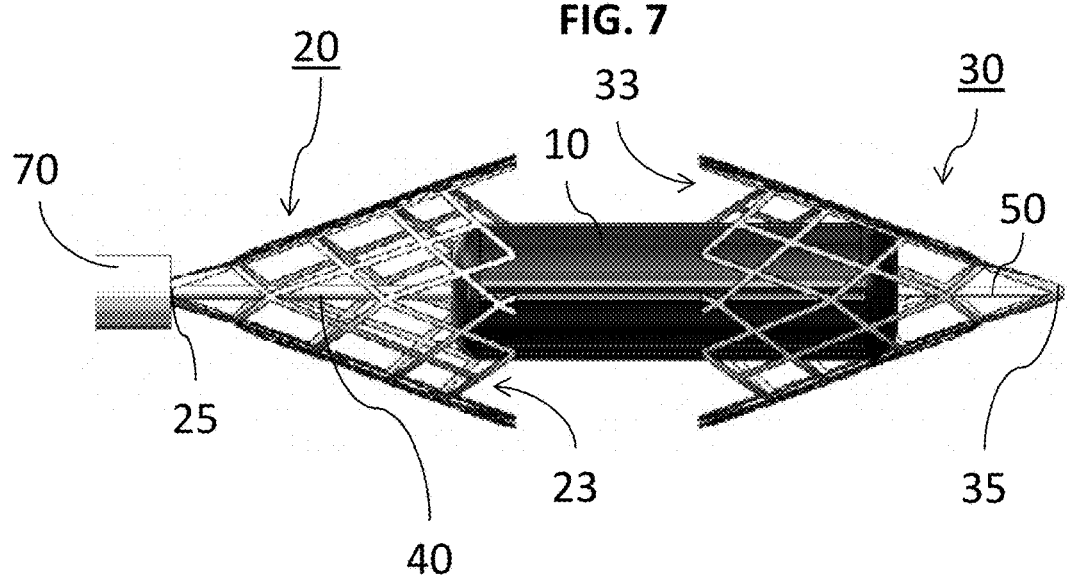
FIG. 7 depicts a side plan view of the device of FIGS. 5-6, wherein the proximal basket is being deployed.
Figure 8:
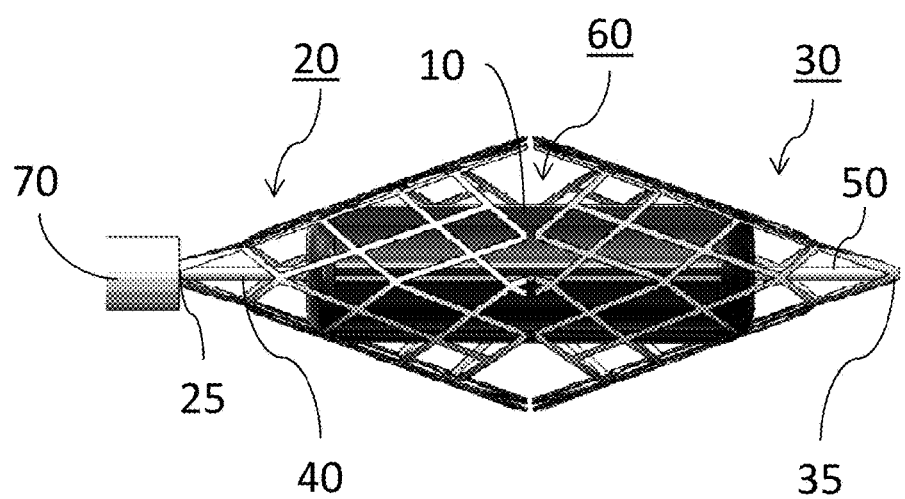
FIG. 8 depicts a side plan view of the device of FIGS. 5-7, wherein each of the proximal and distal baskets are in contact with and capable of removing the blood clot.

In FIG. 7, proximal basket 20 has now been deployed and moved to an expanded stated by moving the microcatheter 70 away from clot 10. Basket 20 is now capable of being positioned to contact the proximal portion of clot 10. In FIG. 8, wire 50 may be moved towards the proximal portion of clot 10 until contacting distal end 45 of hypotube 40. Upon contacting distal end 45, a cage 60 can be formed between each basket 20 and 30. Specifically, since baskets 20 and 30 have been expanded and/or positioned with regards to respect to proximal and distal portions of clot 10 and drawn towards the other, they effectively assemble to form a cage 60 around clot 10 for capturing and removing the clot from the vasculature. Once the cage 60 is formed, the clot 10 can be safely removed from the vasculature. Since the clot 10 is now being pulled from multiple opposed directions, lesser stresses are placed on the blood vessel wall where the clot 10 may have been secured and particles of clot 10 are prevented from entering the bloodstream thereby reducing the risk of injury to the patient.

In certain embodiments, adjusting the size of basket 30 can be achieved by the operator or physician controlling the hypotube 40 and/or wire 50 relative to the other. For example, the hypotube 40 and/or wire 50 may have a plurality of predefined notches or positions associated with respective volumes of basket 30 and/or 20. In this respect, the operator can move an alignment mechanism between respective notches or positions of hypotube 40 and/or wire 50 to easily and precisely adjust the volume of a respective basket.

Figure 9:
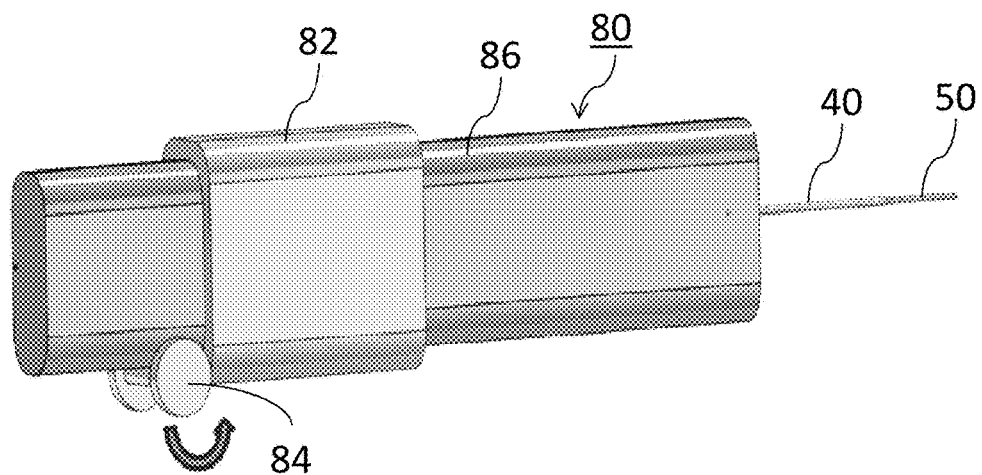
FIG. 9 is an exemplary depiction of an adjustable handle for use with one embodiment of the dual basket device.
Figure 10:
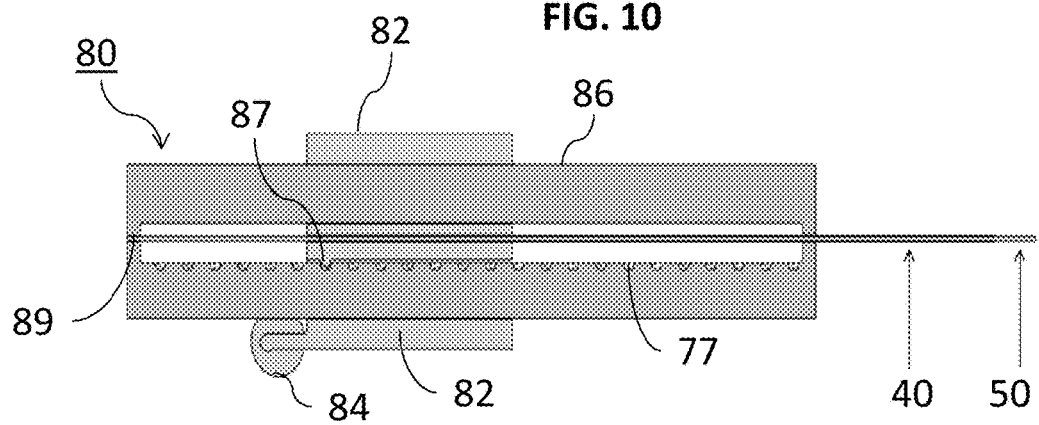
FIG. 10 is side plan cross-section view of the handle of FIG. 9.

As seen in FIG. 9, adjustment of baskets 20 and/or 30 between being stowed, deployed, and/or basket volume can be controlled from a handle 80 operatively connected to hypotube 40 and wire 50. Handle 80 can include a body 86 with a slidable member 82 slidably attached thereon. Member 82 may be operatively attached to an adjustment mechanism 84 through one or more interlinking members. Mechanism 84 may be a rounded axial member and capable of rotating about an axis in a manner that can cause member 82 to move when mechanism 84 is rotated. In certain embodiments, mechanism 94 can act as a thumb wheel to directly drive 82. As shown in FIGS. 9-10, mechanism 84 may be constructed from one or more outer rotational members interconnected by an axial member that is rotatably connected to a lower attachment of member 82. Mechanism 84 can be externally positioned on and detachably connected to member 82. Rotating the axial member of mechanism 84 can cause member 82 to be moved along body 86. In turn, moving member 82 can cause hypotube 40 to be moved thereby incrementally adjusting basket 30 between one of a plurality of different volumes or shapes and deploying basket 30 about clot 10.

This can be more clearly seen in FIG. 10 where a side-plan cross-section view is shown of handle 80 assembled with hypotube 40 and wire 50. Hypotube 40 is secured within 82, and wire 50 is secured within 86 at rear portion 89. Body 86 may also include one or a series of indentations, channels, grooves, or notches 77. Mechanism 82 may further include an extruded member 87 (such as a ball spring plunger) that is operable to move between and land within respective notches 77. It is understood that in certain embodiments, causing mechanism 82 to move incrementally between notches 77 distally away from rear portion 86 can cause basket 30 to be deployed distal of clot 10 and/or be adjusted between one of a plurality of different volumes and/or shapes.

Each notch 77 may be separated a distance and aligned to receive corresponding notch 87 of member 82. In certain embodiments, handle 80 includes a series of notches 87 corresponding to predetermined sizes of basket 30. For example, sliding 82 between a first notch and a second notch may cause corresponding basket 30 to expand from a first volume to a second volume. The solution of device 100 is not limited to the foregoing approaches to adjustment and other modes of adjustment are also contemplated for use with device 100 as needed or required.

FIG. 11 depicts a schematic overview of one exemplary method 200 of using device 100. Specifically, the method can include step 210 where device 100 may be introduced to a distal region of clot 10 and wire 50 may be moved causing distal basket 30 to move and expand away from the clot 10 and microcatheter 70. In certain examples, moving the hypotube 40 towards the distal basket 30 can cause the spokes 44 pivotally connected to struts 34 of basket 30 to expand the distal basket 30 from being collapsed within or along hypotube 40. In step 220, wire 50 can be moved until the distal basket 30 captures the distal portion of the clot 10. In step 230, the microcatheter 70 can be moved proximally away from distal basket 30 and clot 10 causing proximal basket 20 to move from a collapsed state to an expanded state. In step 240, wire 50 can be moved until contacting a distal end of hypotube 40 thereby forming cage 60 around clot 10, cage 60 being formed between the opposed basket frames of baskets 20 and 30. In other words, the open ends 23 and 33 of baskets 20 and 33 may now be in communication with each other to form cage 60 about clot 10. In step 250, once cage 60 is formed between baskets 20 and 30, clot 10 can be safely removed from the vasculature.

Turning to FIG. 12 is a schematic overview of deploying the one of the herein disclosed baskets of the multi-basket clot capturing device 100. The method can include step 310, wherein a frame of a basket, such as basket 20 or 30, is expanded about a first portion of clot 10. The frame of the respective basket may be slidably axially connected to hypotube 40 and/or wire 50. In step 320, the frame of the respective basket can be expanded by sliding outwardly a distal end of the hypotube 40 along the wire 50 when the frame is collapsed and aligned with the hypotube 40 and/or wire 50. The basket may be collapsed completely or partially within microcatheter 70 and/or hypotube 40. In step 330, a plurality of spokes 44 can be pivoted radially outward from hypotube 40 as the hypotube 40 slides along the wire 50 in a predetermined direction (e.g. distally) away from clot 10, spokes 44 being attached between a distal end of hypotube 40 and struts of the basket that form its frame. In turn, the frame of the basket is caused to expand and be ready to surround and capture a respective portion of clot 10.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed examples, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method for removing a clot from vasculature of a patient, comprising the steps of:
   introducing a clot capturing device into a region of interest of the vasculature, the device comprising a distal basket connected to a wire and a proximal basket connected to a hypotube that is axially and slidably connected to the wire, the distal basket being operable to be positioned distal of and capture a distal portion of the clot and a proximal basket, each basket comprising a closed end and an open end and capable of moving from a collapsed state to an expanded state;
   distally moving, relative to the hypotube, the wire connected to the distal basket distal to the clot thereby causing the distal basket to be positioned distal of the clot and expand to the expanded state away from a microcatheter connected to the wire and hypotube;
   proximally moving the wire until the distal basket captures the distal portion of the clot; then
   distally moving the hypotube causing the proximal basket of the clot capturing device to be positioned proximal of the clot and expand to the expanded state, the proximal basket being operable to be positioned proximal of the clot and to capture a proximal portion of the clot; and
   proximally moving the wire connected to the distal basket until contacting a distal end of the hypotube forming a cage around the clot between the opposing open ends of the proximal and distal baskets.

2. The method of claim 1, further comprising: removing the clot from the region of interest of the vasculature.

3. The method of claim 1, further comprising:
   forming a plurality of interstices on at least one of the distal and proximal baskets for capturing the clot;
   pivotally connecting a plurality of spoke members of the hypotube to a plurality of struts of the distal basket; and
   moving the hypotube distally away from the microcatheter, while keeping the wire connected to the distal basket in place, thereby causing the distal basket to expand.

4. The method of claim 3, further comprising: forming a plurality of interstices from the struts.

5. The method of claim 4, further comprising: forming the spoke members by cutting or etching into the distal end of the hypotube.

6. The method of claim 3, further comprising: radially spacing the spoke members about the hypotube.

7. The method of claim 1, further comprising:
   axially connecting the hypotube to a central vertex of the proximal basket; and/or
   axially connecting the wire to a central vertex of the distal basket.

* * * * *